United States Patent
Pedrotti et al.

(10) Patent No.: US 7,341,698 B2
(45) Date of Patent: Mar. 11, 2008

(54) ELECTRICAL EVAPORATOR INCLUDING FAN AND LOUVER STRUCTURE

(75) Inventors: Andrea Pedrotti, Pietramurata (IT); Filippo Stenico, Trento (IT); Fabio Marchetti, Povo (IT); Stefano Deflorian, Martignano (IT); Alessandro Frisanco, Vigolo Vattaro (IT)

(73) Assignee: S.C. Johnson & Son, Inc., Racine, WI (US)

( * ) Notice: Subject to any disclaimer, the term of this patent is extended or adjusted under 35 U.S.C. 154(b) by 607 days.

(21) Appl. No.: 10/267,417

(22) Filed: Oct. 9, 2002

(65) Prior Publication Data

US 2003/0194355 A1    Oct. 16, 2003

Related U.S. Application Data

(60) Provisional application No. 60/371,162, filed on Apr. 10, 2002.

(51) Int. Cl.
*A61L 9/12* (2006.01)
*F24F 6/08* (2006.01)

(52) U.S. Cl. .............. 422/123; 422/124; 422/125; 239/34; 239/44; 392/390; 392/394; 392/395

(58) Field of Classification Search ............ 422/123, 422/124, 125, 5, 305, 306, 392; 239/34, 239/44; 392/390, 392, 394, 395
See application file for complete search history.

(56) References Cited

U.S. PATENT DOCUMENTS

| | | | |
|---|---|---|---|
| 2,828,953 A | 4/1958 | Hartmann | 261/30 |
| 3,633,881 A | 1/1972 | Yurdin | |
| 3,747,902 A | 7/1973 | Bailey | 261/30 |
| 3,804,592 A | 4/1974 | Garbe | 21/121 |
| 3,948,445 A | 4/1976 | Andeweg | 239/53 |
| 4,166,087 A | 8/1979 | Cline et al. | |
| 4,173,604 A | 11/1979 | Dimacopoulos | 261/30 |
| 4,396,557 A | 8/1983 | DeLuca | |
| 4,816,973 A | 3/1989 | Atalla et al. | 362/226 |
| 4,931,224 A * | 6/1990 | Holzner, Sr. | 261/30 |
| 5,081,104 A | 1/1992 | Orson, Sr. | 512/3 |
| 5,114,625 A | 5/1992 | Gibson | 261/30 |

(Continued)

FOREIGN PATENT DOCUMENTS

DE    40 33 926 A1    3/1990

(Continued)

OTHER PUBLICATIONS

Communication dated May 10, 2007, of notice of opposition for corresponding European application, with English translation thereof.

*Primary Examiner*—Gladys J P Corcoran
*Assistant Examiner*—Sean E. Conley (57) ABSTRACT

An evaporator, for use with a bottle containing a substance to be evaporated and a wick that has its lower portion disposed within the bottle and its upper portion protruding from the bottle, includes a housing in which the bottle is retained, a fan, disposed within the housing, for creating an airstream, and a louver structure, disposed downstream of the fan, for directing the airstream created by the fan upwardly and away from the upper portion of the wick. Preferably, the louver structure includes a plurality of louvers inclined at an angle between about 20 degrees to about 60 degrees relative to horizontal.

24 Claims, 11 Drawing Sheets

U.S. PATENT DOCUMENTS

| | | | |
|---|---|---|---|
| 5,484,086 A | 1/1996 | Pu | 222/187 |
| 5,601,636 A | 2/1997 | Glucksman | 96/63 |
| 5,647,053 A | 7/1997 | Schroeder et al. | |
| 5,932,147 A | 8/1999 | Chen | 261/30 |
| 6,287,191 B1 * | 9/2001 | Barker, II | 454/248 |
| 6,319,117 B1 * | 11/2001 | Moore | 454/328 |
| 6,321,556 B1 * | 11/2001 | Tesche et al. | 62/285 |
| 6,361,752 B1 * | 3/2002 | Demarest et al. | 422/306 |
| 6,413,302 B1 | 7/2002 | Harrison et al. | 96/63 |
| 6,680,028 B1 * | 1/2004 | Harris | 422/122 |
| 2001/0053283 A1 * | 12/2001 | Levine et al. | 392/395 |
| 2003/0063902 A1 | 4/2003 | Pedrotti et al. | 392/395 |

FOREIGN PATENT DOCUMENTS

| | | |
|---|---|---|
| DE | 4033926 | 10/1991 |
| JP | 09145192 A * | 6/1997 |
| WO | WO 00/69479 | 11/2000 |
| WO | WO 0069479 | 11/2000 |

* cited by examiner

ELECTRICAL EVAPORATOR INCLUDING FAN AND LOUVER STRUCTURE

RELATED APPLICATION

This application claims the benefit of U.S. Provisional Patent Application No. 60/371,162, filed Apr. 10, 2002.

BACKGROUND OF THE INVENTION

1. Field of the Invention

The present invention relates generally to an electrical evaporator for use with liquid formulations containing a chemical active such as an insecticide, a fragrance, an odor eliminator, or the like, and, in particular, to an electrical evaporator including a fan and a louver structure that helps to achieve a beneficial distribution of the chemical active within a surrounding environment, such as a room.

2. Description of the Related Art

Plug-in electrical evaporators for dispersing chemical actives such as insecticides and fragrances are well known in the art. For the most part, however, these known evaporators fail to achieve an optimal distribution of the chemical active within their surrounding environment. Insecticides, for example, should be concentrated in areas where insects are most likely to come into contact with a person's skin. Fragrances, on the other hand, should be most concentrated at nose level. We have found that known plug-in evaporators generally undersaturate the "living areas" of a room where the chemical active is most likely to come in contact with a person's skin or nose, and oversaturate the non-living areas of a room, such as the floor, ceiling, and walls. This results in a waste of chemical active and a decrease in the overall effectiveness of the evaporator.

SUMMARY OF THE INVENTION

The present invention provides an electrical evaporator that produces a beneficial distribution of the chemical active within a surrounding environment.

According to one aspect of the invention, an evaporator, for use with a bottle containing a substance to be evaporated and a wick that has its lower portion disposed within the bottle and its upper portion protruding from the bottle, includes (i) a housing for retaining the bottle, (ii) a fan, disposed within the housing, for creating an airstream, and (iii) a louver structure, disposed downstream of the fan, for directing the airstream created by the fan upwardly and away from the upper portion of the wick.

In another aspect, the present invention relates to an evaporator including (i) a bottle containing a substance to be evaporated, (ii) a wick, having a lower portion disposed within the bottle and an upper portion protruding from the bottle, for drawing the substance to be evaporated from the bottle toward the upper portion of the wick, (iii) a housing in which the bottle is retained, (iv) means, within the housing, for creating an airstream, and (v) means for directing the airstream upwardly and away from the upper portion of the wick.

In still another aspect, the present invention relates to a plug-in evaporator for dispersing a chemical active into a surrounding environment. The evaporator includes (i) a bottle containing a liquid formulation including at least one chemical active, (ii) a wick, having a lower portion disposed within the bottle and an upper portion protruding from the bottle, for drawing the liquid formulation from the bottle toward the upper portion of the wick, (iii) a housing in which the bottle is detachably retained, (iv) an electrical heating device, disposed within the housing at a position proximate to the upper portion of the wick, for enhancing evaporation of the liquid formulation from the upper portion of the wick, (v) a fan, disposed within the housing, for creating an airstream that entrains the evaporated liquid formulation, and (vi) an electrical plug, extending from the housing, for supplying power to the heating device and the fan and for supporting the evaporator in a wall outlet. The housing includes a plurality of louvers located downstream from the fan for directing the airstream created by the fan upwardly and away from the heating device and the upper portion of the wick. Preferably, the louvers are inclined at an angle between about 20 degrees to about 60 degrees relative to horizontal when the evaporator is in an upright position.

A better understanding of these and other features and advantages of the invention may be had by reference to the drawings and to the accompanying description, in which preferred embodiments of the invention are illustrated and described.

BRIEF DESCRIPTION OF THE DRAWINGS

Throughout the figures, like or corresponding reference numerals have been used for like or corresponding parts.

DESCRIPTION OF THE PREFERRED EMBODIMENTS

An evaporator 100 according to a preferred embodiment of the present invention is illustrated in FIGS. 1-11.

Figure 1:
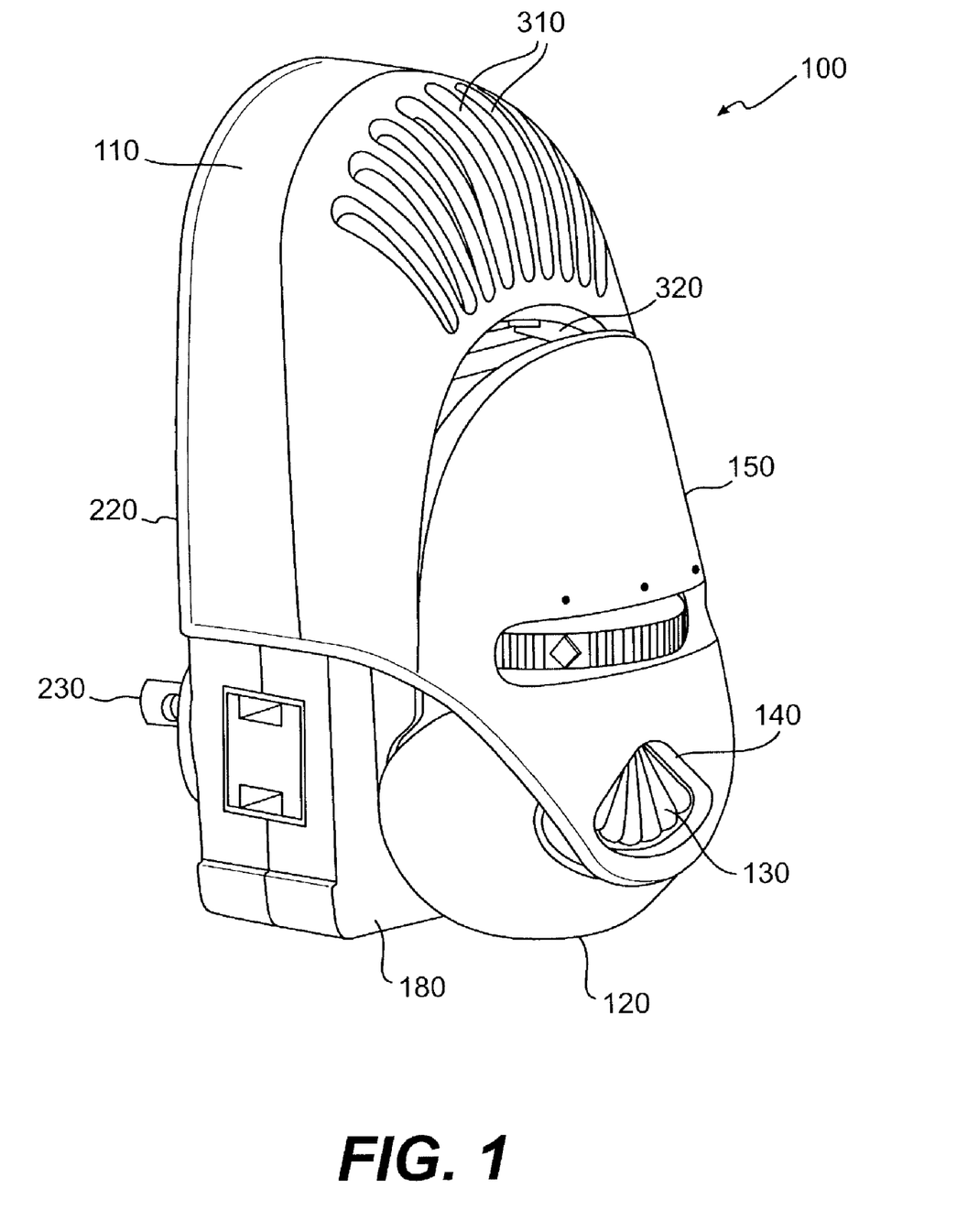
FIG. 1 is a perspective view of an evaporator according to a preferred embodiment of the present invention.

As shown in FIG. 1, the evaporator 100 comprises a multi-piece housing 110 in which a bottle 120 is detachably retained. The bottle 120 contains an evaporable substance (not shown), such as, for example, a liquid formulation including a chemical active such as an insecticide, fragrance, odor eliminator, or the like. The term "bottle" is used herein in its broadest possible sense, including any receptacle, container, pouch, etc., capable of holding a liquid formulation. A raised pattern 130 on one side of the bottle is engaged by an opening 140 in a front shell 150 of the evaporator housing 110, while a similar raised pattern 160 (shown in FIG. 6) on an opposite side of the bottle 120 is engaged by a recess 170 (shown in FIG. 3) in a middle shell 180, in order to secure the bottle 120 within the evaporator 100. The front shell 150 is sufficiently pliant so that pulling the bottle 120 in a downward direction causes the raised patterns 130, 160 to release from the opening 140 in the front shell 150 and the recess 170 in the middle shell 180, respectively, thereby enabling removal of the bottle 120 from the evaporator 100. Alternatively, the neck portion of the bottle may be designed to snap or screw into the evaporator housing. Suitable refill bottles are available in a wide variety of liquid formulations from S.C. Johnson & Son, Inc., of Racine, Wis., under the GLADE® PLUGINS® and RAID® brand names.

Figure 3:
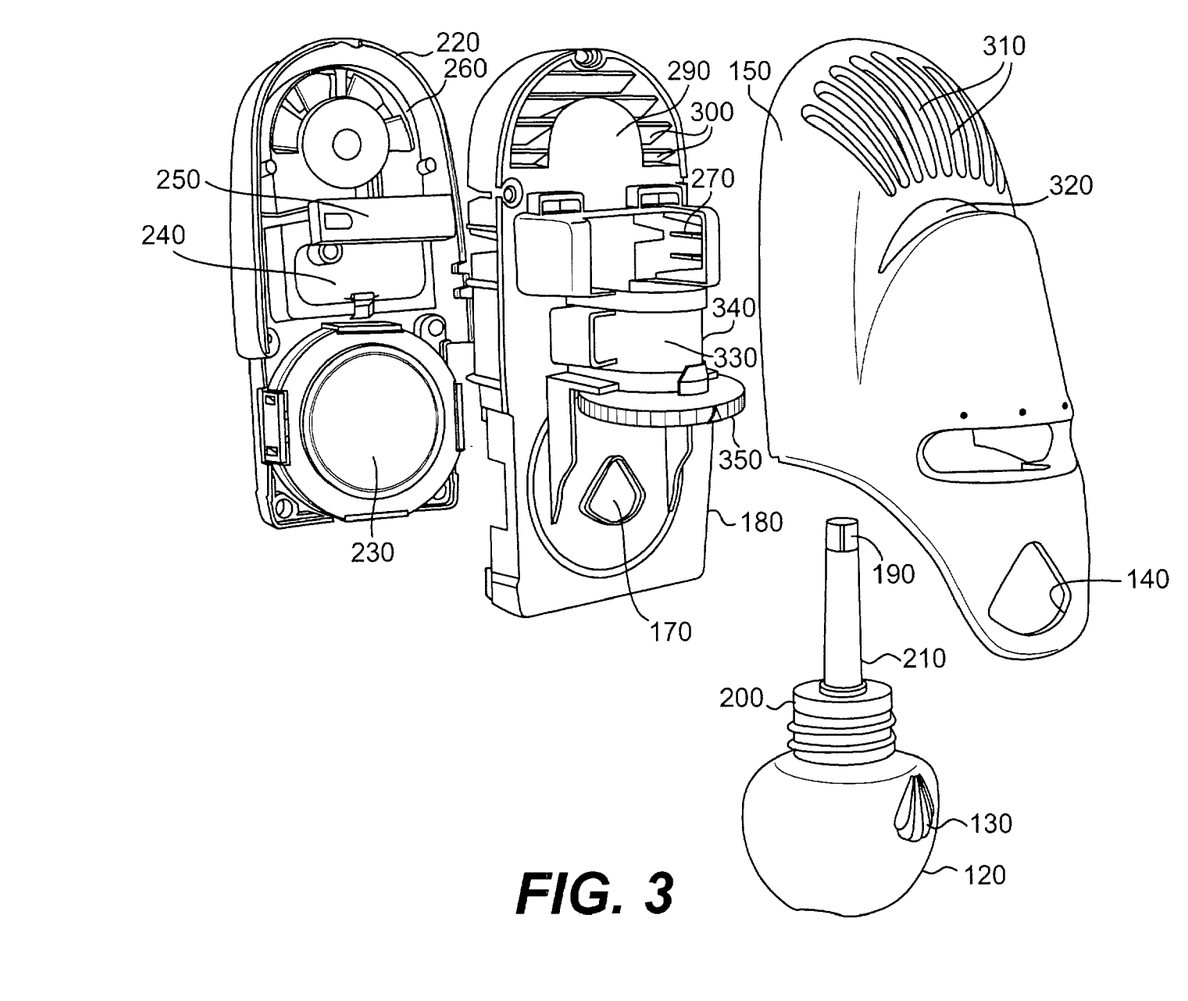
FIG. 3 is an exploded assembly view of the evaporator shown in FIG. 1.
Figure 4:
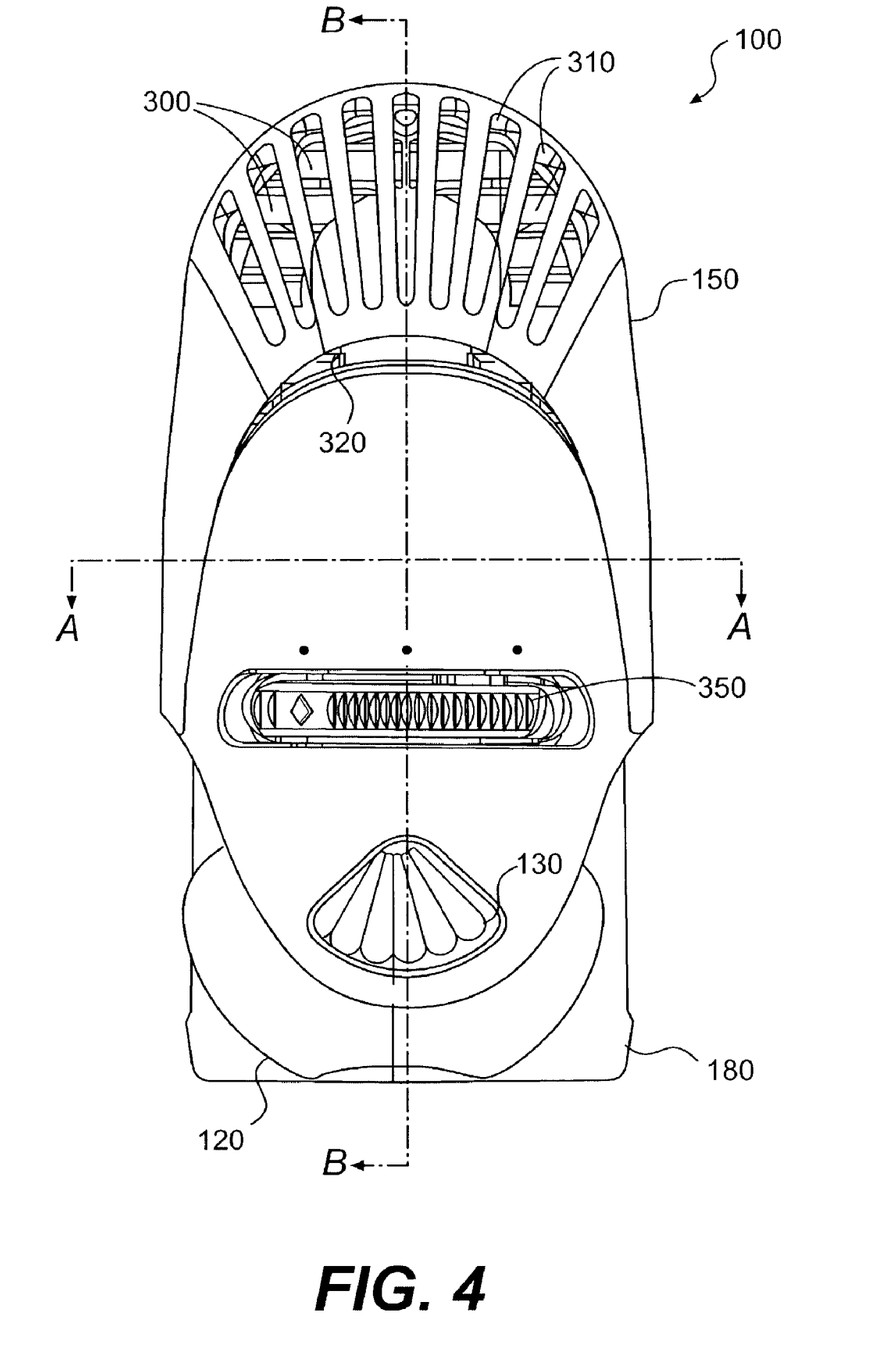
FIG. 4 is a front elevation view of the evaporator shown in FIG. 1, with the intensity setting on low.

As shown in FIG. 3, the bottle 120 includes a wick 190 for drawing the liquid formulation out of the bottle 120 and toward an upper portion of the wick 190. A lower portion of the wick 190 is immersed in the liquid formulation, and the upper portion of the wick 190 protrudes above the neck of the bottle 120. Preferably, the wick 190 is positioned within the bottle 120 by a cap 200 which includes a sheath 210 that encases the upper portion of the wick 190, except for an open area near the tip of the wick 190. Alternatively, a cap without a sheath can be utilized. Preferably, the wick is about 7 mm in diameter and is constructed of ultra high molecular weight high density polyethylene.

In the preferred embodiment illustrated in FIGS. 1-10, the evaporator housing 110 comprises three shells—the front and middle shells 150, 180 noted above and a back shell 220—which are fastened together by heat-staking or any other suitable fastening means, including, for example, rivets, press fit, snap fit, screws, ultrasonic welding, adhesives, or the like. The electrical components (discussed in more detail below) of the evaporator 100 are housed within the space enclosed by the middle and back shells 180, 220.

Figure 2:
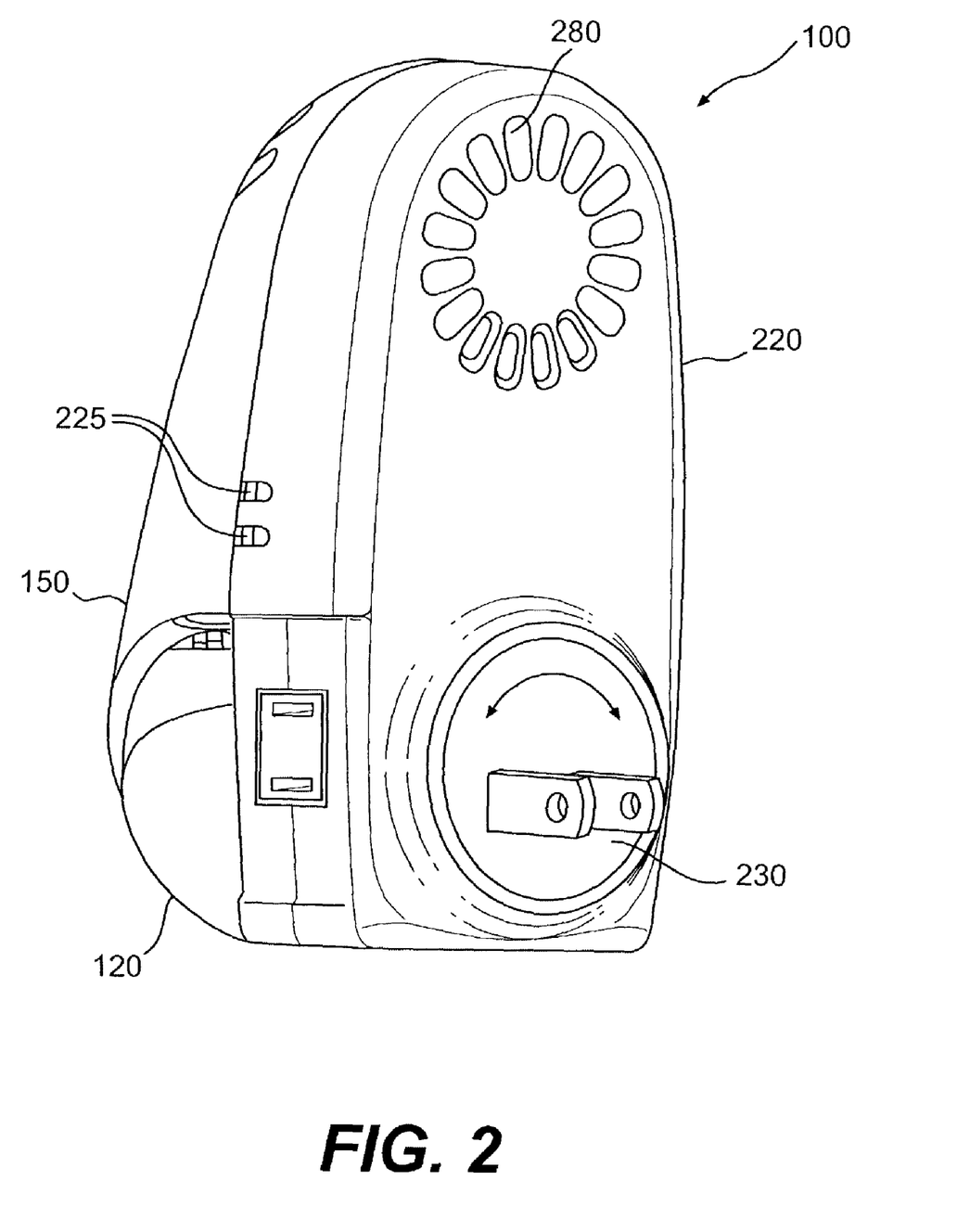
FIG. 2 is a rotated perspective view of the evaporator shown in FIG. 1.

Referring to FIG. 2, the back shell 220 contains a circular opening in which a known electrical plug assembly 230 is seated. The plug 230 serves the dual purpose of supplying power to the electrical components of the evaporator 100 and also supporting the evaporator 100 in a wall outlet (not shown). Preferably, the plug assembly 230 is rotatable 360 degrees in order to support the evaporator 100 in an upright position in both horizontal and vertical wall outlets. Advantageously, the plug assembly 230 can be provided with an extra outlet which, as illustrated in FIG. 1, is located on the side of the evaporator 100 when the evaporator is plugged into a vertical wall outlet, and on the bottom of the evaporator 100 when the evaporator is plugged into a horizontal wall outlet (not shown).

As schematically illustrated in FIG. 3, the plug assembly 230 is electrically connected to a circuit board 240, which, in turn, is electrically connected to a heating device 250 and, preferably, also to a fan unit 260. The heating device 250 is disposed adjacent to a window 270 in the middle shell 180 which faces the tip of the wick 190 when the bottle 120 is inserted in the evaporator 100. Heating the wick 190 enhances the rate at which the liquid formulation evaporates into the surrounding environment, as described more fully below. Preferably, the heating device 250 is a 1.9 kΩ, 7 W metal oxide resistor potted in a ceramic block. The resistor preferably has PTC (positive temperature coefficient) characteristics, meaning that its resistance value increases slightly as the resistor heats up. A suitable resistor is available from Great Land Enterprise Co., Ltd., of Shenzhen, China, for example. Alternatively, the heating device 250 can comprise one or more other types of resistor heaters, a wire-wound heater, a PTC heater, or the like.

The fan unit 260 is disposed within an upper portion of the housing 110. The back shell 220 includes air inlets 280 (shown in FIG. 2) for supplying air to the fan unit 260. As described more fully below, the fan unit 260 creates an airstream that entrains the evaporated liquid formulation and assists in the dispersion of the chemical active into the surrounding environment. Preferably, the flow rate of the fan unit 260 within the evaporator 100 is approximately 0.5 cubic feet per minute, and the fan speed is approximately 2800-3800 RPM. A suitable fan unit 260 is a 12 V, DC, brushless fan, such as available from Power Logic Tech. Inc., of Tapei-Hsien, Taiwan. Alternatively, other DC or AC fans could be utilized, with appropriate adjustments to the circuit board 240, which is described more fully below.

Figure 11:
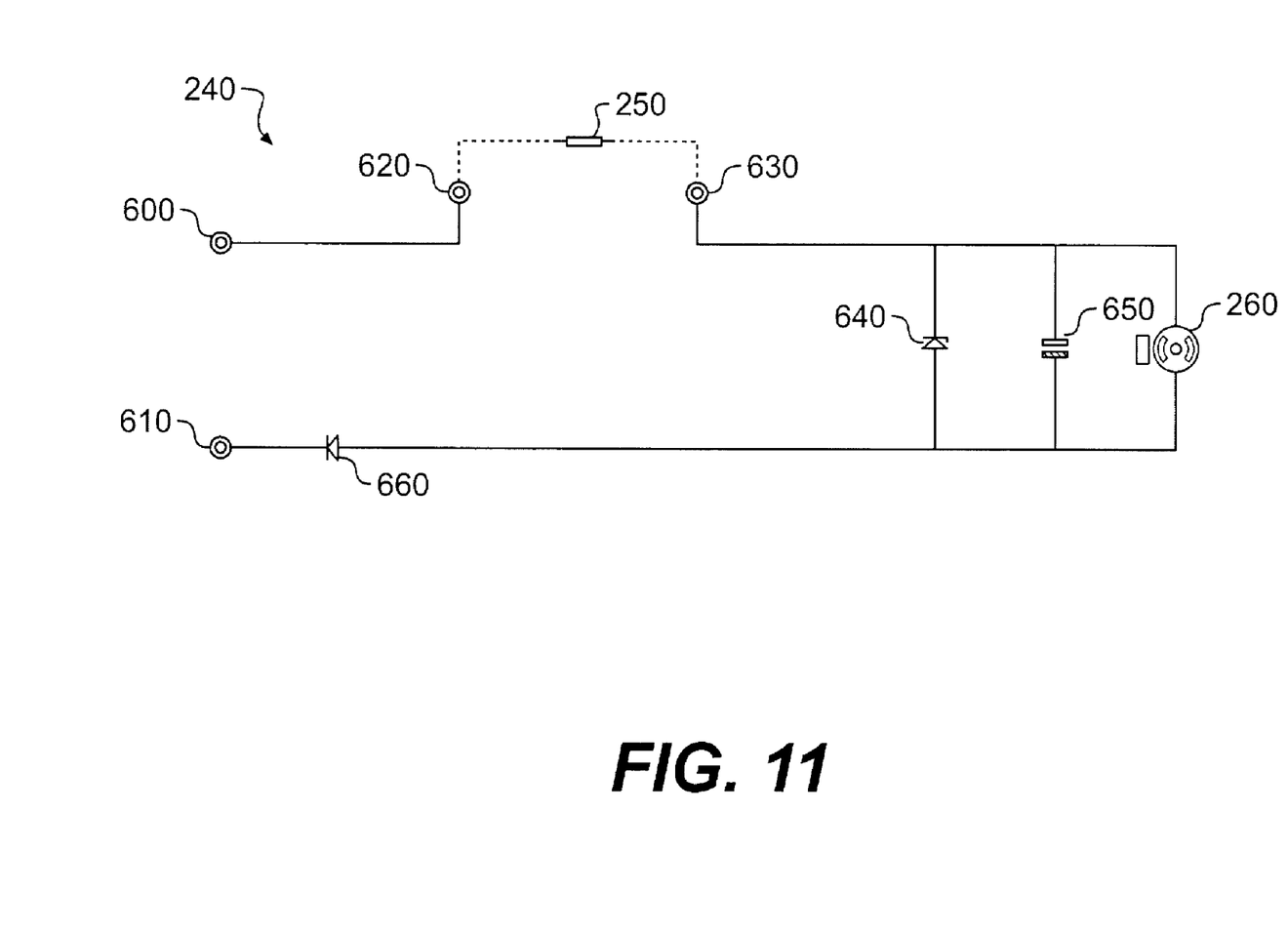
FIG. 11 is a schematic diagram of a preferred electrical circuit for the evaporator shown in FIG. 1.

FIG. 11 is a schematic diagram of a preferred circuit board 240 for the evaporator 100. Preferably, the circuit board 240 is constructed of a flame-rated material. The circuit board 240 includes pins 600, 610 that connect to bus bars (not shown) of the plug assembly 230. The voltage applied across the pins 600, 610 is 120 V, at a frequency of 60 Hz. The heating device 250 is connected to the circuit board 240 by a pair of rivets 620, 630. Connected in parallel are (i) a 15 V, 1.3 W Zener diode 640, (ii) a 22 µF, 50 V aluminum electrolytic capacitor 650, rated for a temperature of 105° C., and (iii) the fan unit 260. The circuit board 240 also includes a 1N 4007 diode 660. The power consumption across the entire circuit is about 3.5 W to about 4.0 W. Those skilled in the art will appreciate that numerous alternative circuit configurations are also possible.

Figure 10:
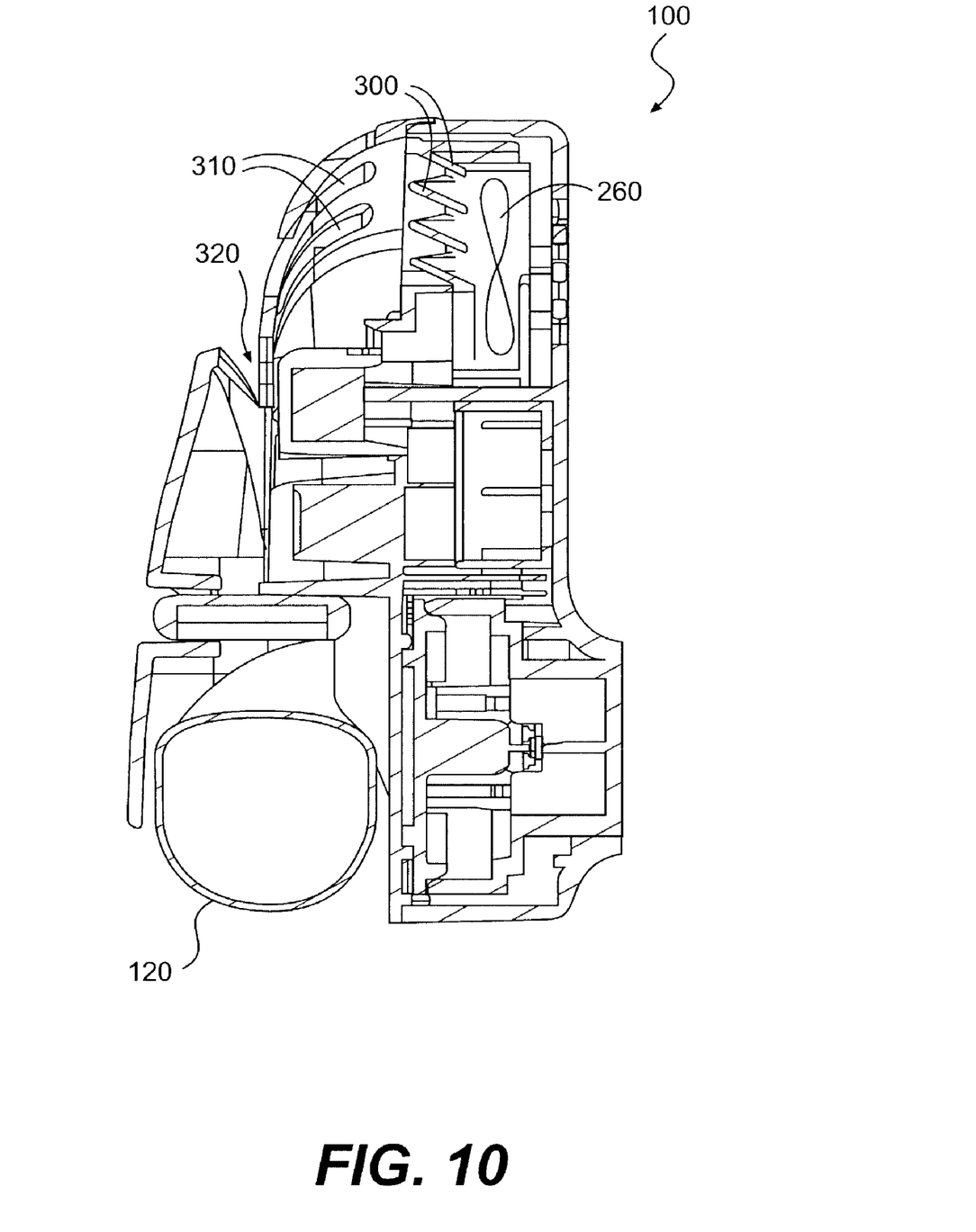
FIG. 10 is a cross-sectional view taken along section line E-E in FIG. 7.

Immediately downstream of the fan unit 260 is a louver structure 290, shown in FIG. 3, comprising at least one louver and, more preferably, a plurality of louvers 300. Preferably, the louver structure 290 is an integral part of the middle shell 150, but it can also be provided separately from the middle shell 150. As illustrated in FIGS. 3 and 10, the louvers 300 are angled upwardly and away from the heating device 250 and the upper portion of the wick 190, preferably at an angle between about 20 degrees to about 60 degrees relative to horizontal when the evaporator 100 is in an upright position.

The optimum louver angle varies depending on such factors as the fan speed and the air exchange rate within the room in which the evaporator 100 is located. In rooms with relatively low air exchange rates (e.g., between about 0.6 to about 1.2 exchanges per hour), a louver angle of about 40 degrees to about 45 degrees relative to horizontal is preferred. In rooms with higher air exchange rates, a louver angle of about 25 degrees to about 30 degrees relative to horizontal is preferred.

The middle shell 180 is shaped so as to direct the airstream created by the fan unit 260 through the louvers 300. Notably, the middle shell 180 does not permit stray currents of air to recirculate within the housing 110, where those currents could have an undesirable cooling effect on the heating device 250. A pair of openings 225 (shown in FIG. 2) in the side of the evaporator 100 helps to achieve proper air circulation through the evaporator.

The front shell 150 includes a plurality of vents 310 through which the airstream exits the evaporator 100 after passing through the louvers 300. As the airstream exits the evaporator 100 through the vents 310, it entrains the evaporated liquid formulation, which rises from the wick 190 through an opening 320 in the front shell 150 below the vents 310.

Tests have demonstrated that an evaporator constructed in accordance with the present invention disperses higher concentrations of the chemical active within the central "living area" of a room, as opposed to the walls, floor, or ceiling.

Those skilled in the art will appreciate that the benefits of the fan unit 260 and louver structure 290 described above can be achieved even in the absence of a heating device 250.

Optionally, the evaporator 100 also includes an adjustment mechanism 330 that positions the upper portion of the wick 190 with respect to the heating device 250. Preferably, the adjustment mechanism 330 includes a hollow cylindrical portion 340 that surrounds and engages part of the upper portion of the wick 190, preferably at a location where the wick 190 is encased by the sheath 210. The adjustment mechanism 330 also includes a dial portion 350, accessible from outside the evaporator housing 110, for rotating the cylindrical portion 340 about an axis of rotation. The dial portion 350 preferably is formed integrally with the cylindrical portion 340, although it need not be.

Figure 5:
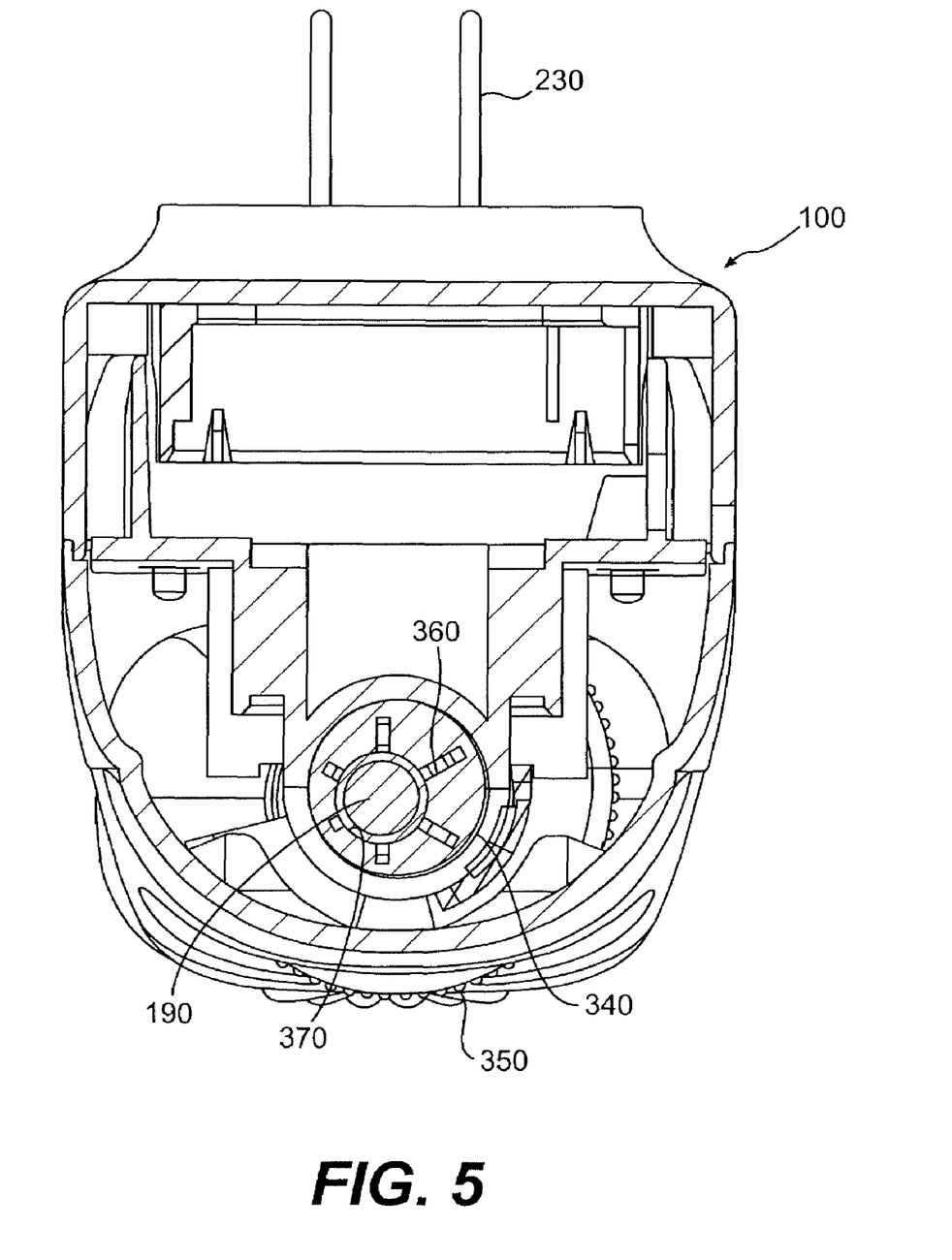
FIG. 5 is a cross-sectional view taken along section line A-A in FIG. 4.
Figure 6:
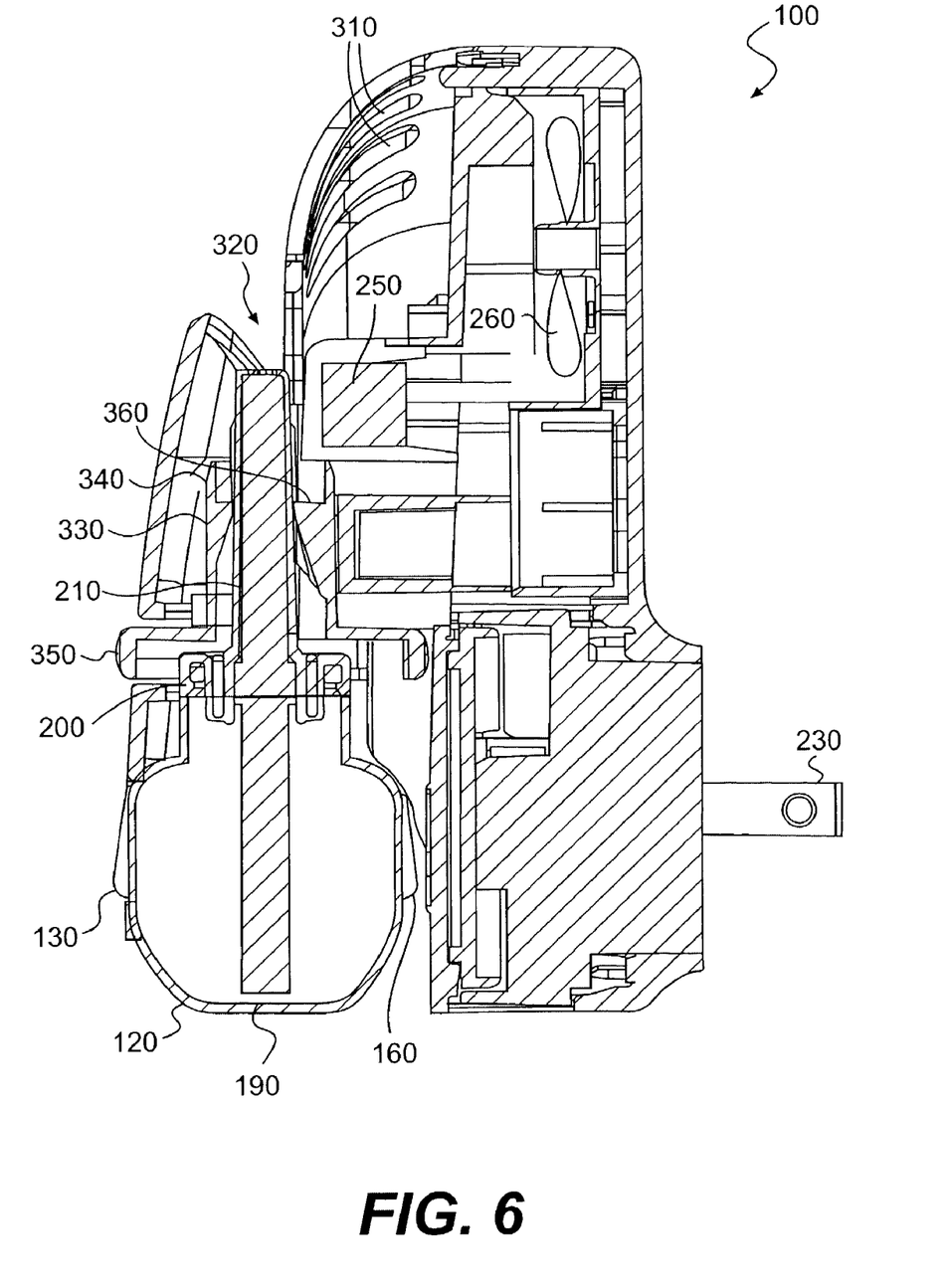
FIG. 6 is a cross-sectional view taken along section line B-B in FIG. 4.

Preferably, as shown in FIG. 5, a plurality of tapered lugs 360 is provided on the inner surface of the cylindrical portion 340. The lugs 360 are widest at their uppermost point, where they come in contact with the wick 190, and narrowest near the bottom of the cylindrical portion 340. At their uppermost point, the lugs 360 define a circular opening 370 that is just large enough for the wick 190 to fit through. The center of this opening 370 is offset relative to the axis of rotation of the cylindrical portion 340.

Figure 7:
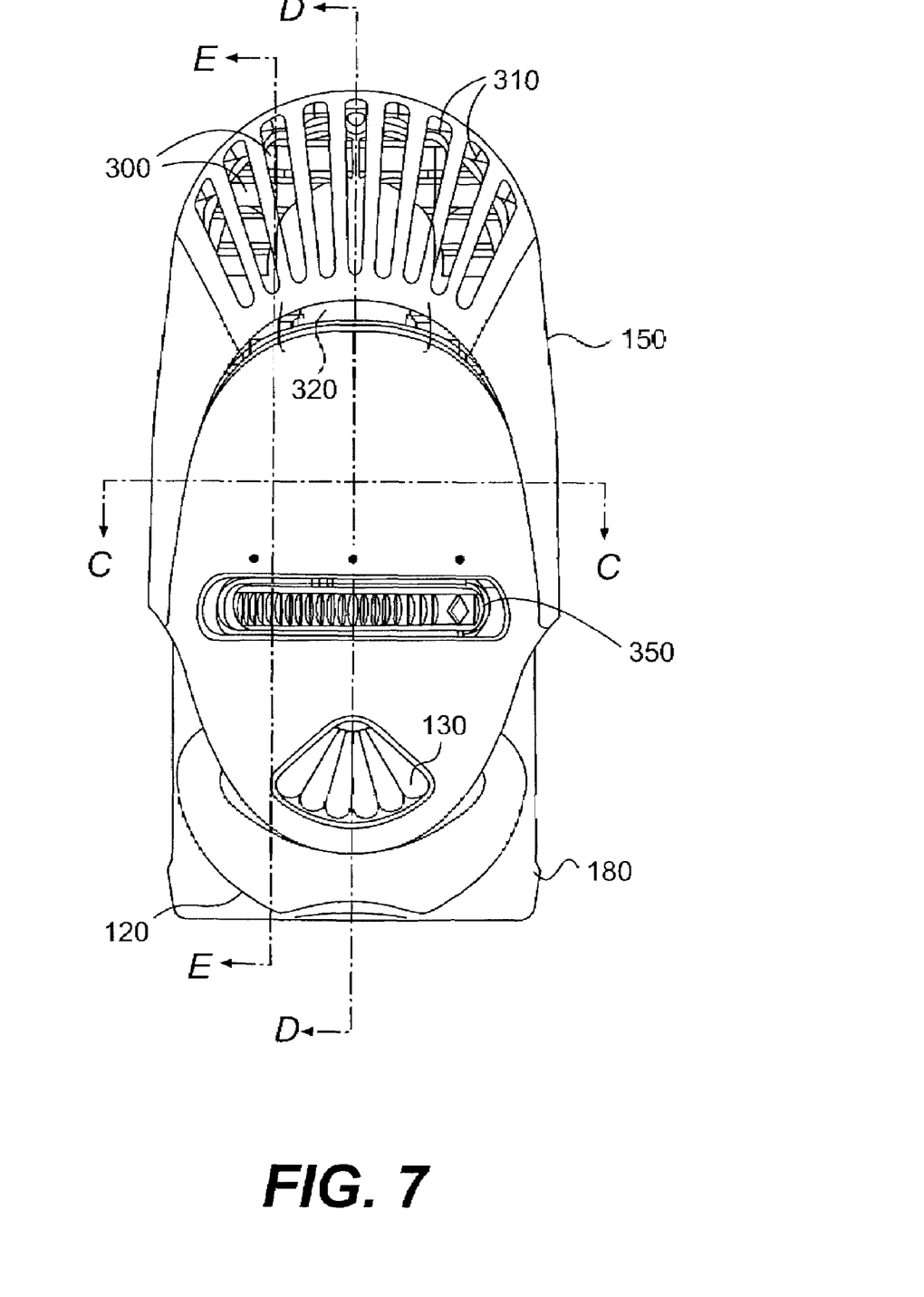
FIG. 7 is a front elevation view of the evaporator shown in FIG. 1, with the intensity setting on high.
Figure 8:
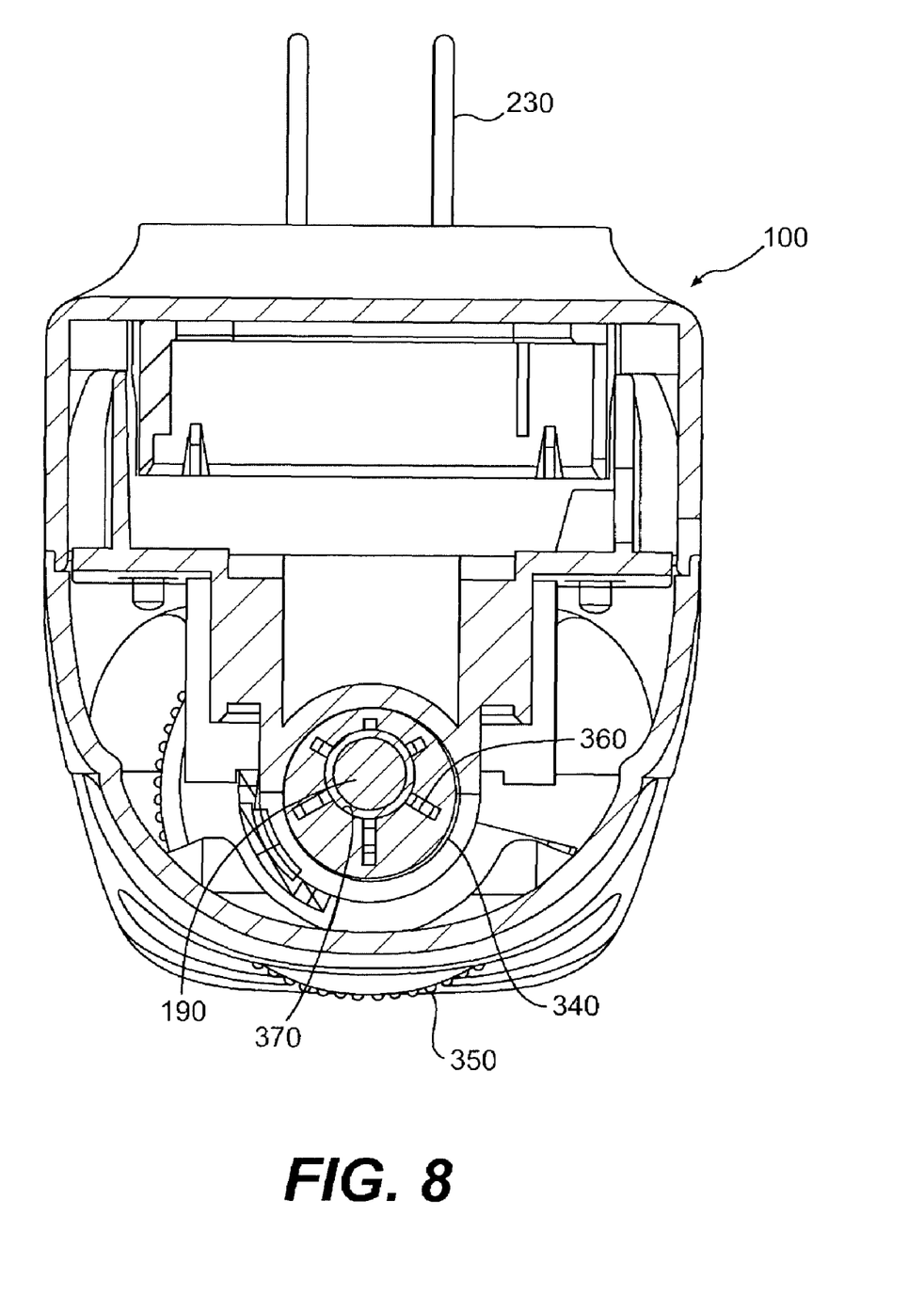
FIG. 8 is a cross-sectional view taken along section line C-C in FIG. 7.
Figure 9:
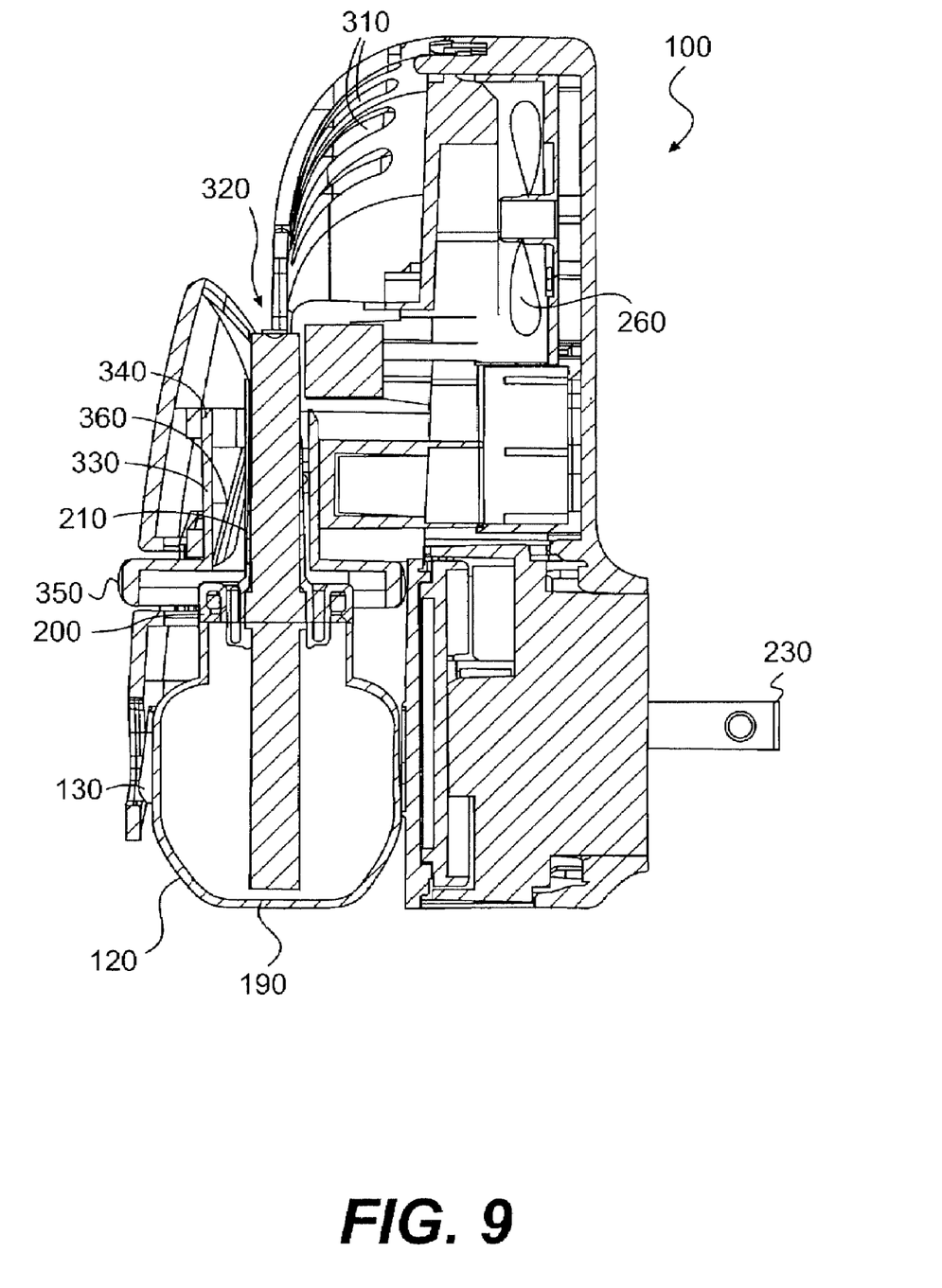
FIG. 9 is a cross-sectional view taken along section line D-D in FIG. 7.

Rotating the dial portion 350 of the adjustment mechanism 330 causes the wick 190 to move toward or away from the heating device 250 in a lateral direction, i.e., in a direction substantially perpendicular to the longitudinal axis of the wick 190. In the minimum intensity setting illustrated in FIGS. 4-6, the axis of the wick 190 is positioned about 6.3 mm from the heating device 250. In this position, the wick is heated to a temperature of about 71-78° C. Rotating the dial portion 350 approximately 75 degrees to the right brings the wick axis to a position that is about 4.4 mm from the heating device 250. At this maximum setting, which is illustrated in FIGS. 7-9, the wick is heated to a temperature of about 85-90° C., thereby resulting in a higher evaporation rate. The evaporator 100 also can be set to an intensity level anywhere in between the minimum and maximum settings. The lateral distance traveled by the wick 190 in moving from the minimum intensity setting to the maximum intensity setting is preferably between about 1 mm and about 3.5 mm. In the particular preferred embodiment described above, the lateral distance traveled by the wick 190 is about 2 mm.

Weight loss tests have demonstrated that the evaporation rate is almost 300 percent higher at the maximum setting than at the minimum setting.

The embodiments discussed above are representative of preferred embodiments of the present invention and are provided for illustrative purposes only. They are not intended to limit the scope of the invention. Although specific structures, dimensions, components, etc., have been shown and described, such are not limiting. Modifications and variations are contemplated within the scope of the present invention, which is intended to be limited only by the scope of the accompanying claims.

INDUSTRIAL APPLICABILITY

The present invention provides an electrical evaporator for use with liquid formulations containing a chemical active such as an insecticide, fragrance, odor eliminator, or the like. The evaporator includes a fan and a louver structure for directing an airstream created by the fan upwardly and away from a wick, which is saturated with the liquid formulation. As the liquid formulation evaporates from the wick, it is entrained in the airstream and dispersed into the surrounding environment. The fan and louver structure help to achieve a beneficial distribution of the chemical active within the surrounding environment, so that the chemical active is more highly concentrated in areas where it is most likely to be effective, and less concentrated in other areas. This results in more efficient use of the chemical active.

We claim:

1. An evaporator, comprising:
a bottle containing a substance to be evaporated;
a wick, having a lower portion disposed within the bottle and an upper portion protruding from the bottle, for drawing the substance to be evaporated from the bottle toward the upper portion of the wick;
a housing for retaining the bottle, the housing formed of separate front, middle and back shells;
a fan, formed within the back shell of the housing, for creating an airstream;
at least one air inlet formed in the back shell of the housing for supplying air to the fan;
a louver structure, disposed downstream of the fan and formed in the middle shell, and including a plurality of louvers positioned at various angles, for directing the airstream created by the fan upwardly and away from the upper portion of the wick; and
at least one vent formed in the front shell of the housing through which the airstream exits the housing, wherein the vent is disposed downstream of both the fan and the louver structure.

2. The evaporator of claim 1, wherein at least one of the plurality of louvers of the louver structure about 20 degrees to about 60 degrees relative to horizontal when the evaporator is in an upright position.

3. The evaporator of claim 1, wherein at least one of the plurality of louvers of the louver structure is inclined at an angle of about 25 degrees to about 30 degrees relative to horizontal when the evaporator is in an upright position.

4. The evaporator of claim 1, wherein at least one of the plurality of louvers of the louver structure is inclined at an angle of about 40 degrees to about 45 degrees relative to horizontal when the evaporator is in an upright position.

5. The evaporator of claim 1, wherein the bottle is detachably retained within the housing.

6. The evaporator of claim 1, wherein the substance to be evaporated is one of an insecticide, a fragrance, or an odor eliminator.

7. The evaporator of claim 1, further comprising an electrical plug for supplying power to the fan and for supporting the evaporator in a wall outlet.

8. The evaporator of claim 7, wherein the electrical plug is rotatable in order to support the evaporator in an upright position in both horizontal and vertical wall outlets.

9. The evaporator of claim 1, further comprising an electrical heating device, disposed within the housing at a position proximate to the upper portion of the wick, for enhancing evaporation of the substance to be evaporated.

10. An evaporator, comprising:
a bottle containing a substance to be evaporated;
a wick, having a lower portion disposed within the bottle and an upper portion protruding from the bottle, for drawing the substance to be evaporated from the bottle toward the upper portion of the wick;
a housing in which the bottle is retained, the housing formed of separate front, middle and back shells;
means formed within the back shell of the housing, for creating an airstream;
means formed in the back shell for supplying air to the means for creating an airstream;

means formed in the middle shell, including a plurality of louvers positioned at various angles, for directing the airstream upwardly and away from the upper portion of the wick; and means formed in the front shell through which the airstream exits the housing.

11. The evaporator of claim 10, wherein at least one of the plurality of louvers of the directing means is inclined at an angle between about 20 degrees to about 60 degrees relative to horizontal when the evaporator is in an upright position.

12. The evaporator of claim 10, wherein at least one of the plurality of louvers of the directing means is inclined at an angle of about 25 degrees to about 30 degrees relative to horizontal when the evaporator is in an upright position.

13. The evaporator of claim 10, wherein at least one of the plurality of louvers of the directing means is inclined at an angle of about 40 degrees to about 45 degrees relative to horizontal when the evaporator is in an upright position.

14. The evaporator of claim 10, wherein the bottle is detachably retained within the housing.

15. The evaporator of claim 10, wherein the substance to be evaporated is one of an insecticide, a fragrance, or an odor eliminator.

16. The evaporator of claim 10, wherein the means for creating an airstream comprises a fan.

17. The evaporator of claim 16, further comprising an electrical plug for supplying power to the fan and for supporting the evaporator in a wall outlet.

18. The evaporator of claim 17, wherein the electrical plug is rotatable in order to support the evaporator in an upright position in both horizontal and vertical wall outlets.

19. The evaporator of claim 10, further comprising an electrical heating device, disposed within the housing at a position proximate to the upper portion of the wick, for enhancing evaporation of the substance to be evaporated.

20. A plug-in evaporator for dispersing a chemical active into a surrounding environment, the evaporator comprising:
    a bottle containing a liquid formulation including at least one chemical active;
    a wick, having a lower portion disposed within the bottle and an upper portion protruding from the bottle, for drawing the liquid formulation from the bottle toward the upper portion of the wick;
    a housing in which the bottle is detachably retained, the housing formed of separate front, middle and back shells;
    an electrical heating device, disposed within the housing at a position proximate to the upper portion of the wick, for enhancing evaporation of the liquid formulation from the upper portion of the wick;
    a fan, formed within the back shell of the housing, for creating an airstream that entrains the evaporated liquid formulation; and
    an electrical plug, extending from the back shell of the housing, for supplying power to the heating device and the fan and for supporting the evaporator in a wall outlet,
    wherein the back shell of the housing includes at least one air inlet for supplying air to the fan, the middle shell of the housing includes a plurality of louvers formed in the middle shell and located downstream from the fan for directing the airstream created by the fan upwardly and away from the heating device and the upper portion of the wick, the louvers being inclined at an angle between about 20 degrees to about 60 degrees relative to horizontal when the evaporator is in an upright position, and at least one vent formed in the front shell of the housing through which the airstream created by the fan exits the housing.

21. The evaporator of claim 20, wherein the louvers are inclined at an angle of about 25 degrees to about 30 degrees relative to horizontal when the evaporator is in an upright position.

22. The evaporator of claim 20, wherein the louvers are inclined at an angle of about 40 degrees to about 45 degrees relative to horizontal when the evaporator is in an upright position.

23. The evaporator of claim 20, wherein the liquid formulation is one of an insecticide, a fragrance, or an odor eliminator.

24. The evaporator of claim 20, wherein the electrical plug is rotatable in order to support the evaporator in an upright position in both horizontal and vertical wall outlets.

* * * * *